US007759115B2

(12) United States Patent
Etheredge, III et al.

(10) Patent No.: US 7,759,115 B2
(45) Date of Patent: Jul. 20, 2010

(54) INCUBATION AND/OR STORAGE CONTAINER SYSTEM AND METHOD

(75) Inventors: Robert W Etheredge, III, Natick, MA (US); Robert P Maloney, Maynard, MA (US); Claude J Ranoux, Winchester, MA (US); Francis G Gleason, Jr., Ashland, MA (US)

(73) Assignee: Bio X Cell, Inc., Winchester, MA (US)

( * ) Notice: Subject to any disclaimer, the term of this patent is extended or adjusted under 35 U.S.C. 154(b) by 520 days.

(21) Appl. No.: 10/360,630

(22) Filed: Feb. 10, 2003

(65) Prior Publication Data

US 2004/0157205 A1 Aug. 12, 2004

(51) Int. Cl.
*C12M 1/24* (2006.01)
*C12M 3/00* (2006.01)
*C12P 19/04* (2006.01)

(52) U.S. Cl. .............. 435/304.1; 435/288.1; 435/307.1; 435/101; 435/1.1; 435/1.2; 600/33; 600/34; 600/35; 604/906

(58) Field of Classification Search .................. 600/33, 600/34, 35; 435/304.1, 288.1, 307.1, 101, 435/1.2, 1.1; 604/906
See application file for complete search history.

(56) References Cited

U.S. PATENT DOCUMENTS 4,839,292 A * 6/1989 Cremonese .............. 435/297.2
4,902,286 A 2/1990 Ranoux
5,135,865 A 8/1992 Ranoux
5,691,194 A * 11/1997 Gordon ................... 435/287.1
5,714,384 A * 2/1998 Wilson et al. ............... 435/401
5,928,935 A * 7/1999 Reuss et al. .............. 435/288.1
6,050,935 A 4/2000 Ranoux
6,642,019 B1 * 11/2003 Anderson et al. ............. 435/41
6,653,124 B1 * 11/2003 Freeman .................. 435/297.1
2004/0029266 A1 * 2/2004 Barbera-Guillem ...... 435/297.5

FOREIGN PATENT DOCUMENTS

EP 0131166 1/1985

OTHER PUBLICATIONS

Unexpected Low Oxygen Tension of Intravaginal Culture, Misao Fukuda, Klyomi Fukuda and Claude Ranoux, Human Reproduction, vol. 11, No. 6, pp. 1293-1295, 1996.
Handbook of In-Vitro Fertilization, Alan Trounson & David K. Gardner, 1993.

* cited by examiner

*Primary Examiner*—William H Beisner
*Assistant Examiner*—Nathan A Bowers
(74) *Attorney, Agent, or Firm*—Young & Thompson

(57) ABSTRACT

A container assembly comprises a vessel for containing a biological medium, gametes and/or one or more embryo(s). The vessel has a $CO_2$ permeable seal and a closure valve device for selective access. A buffer chamber for a $CO_2$ enriched atmosphere cooperates with the vessel and is in communication with the $CO_2$ permeable wall. Such a container assembly is particularly adapted for intravaginal use in which case the permeable seal prevents ingress of vaginal secretions. The buffer chamber mediates the aqueous pH in the vessel after the container assembly is removed from a $CO_2$ enriched environment.

59 Claims, 4 Drawing Sheets

Fig.3
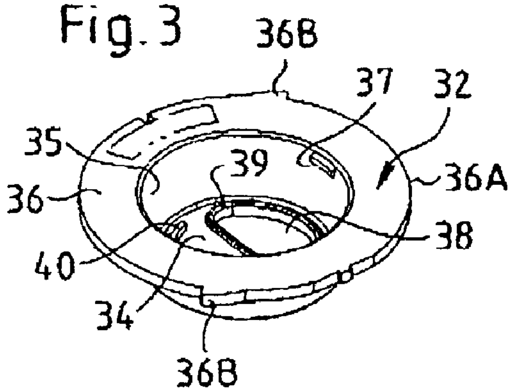
Fig.4
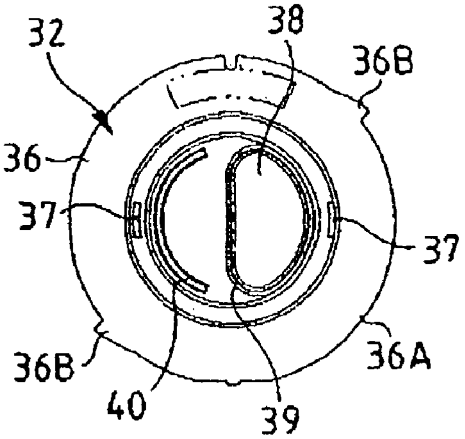
Fig.5
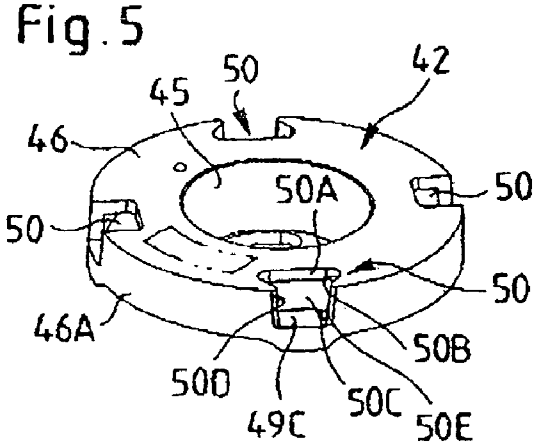
Fig.6
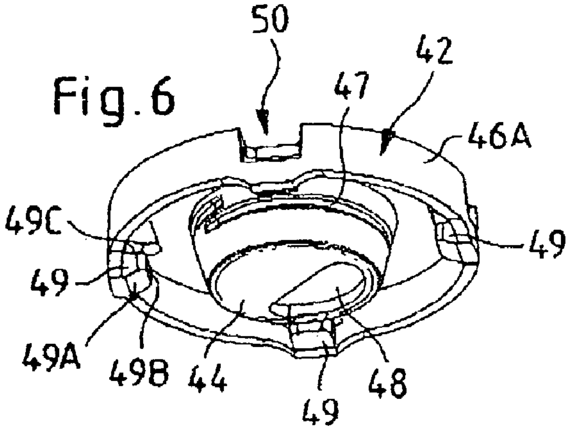
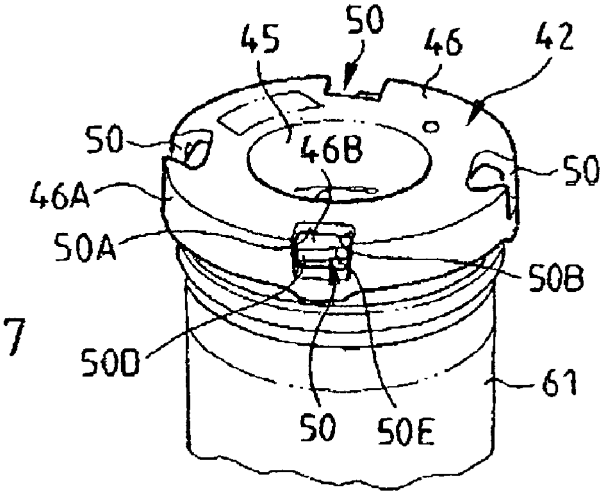
Fig.7

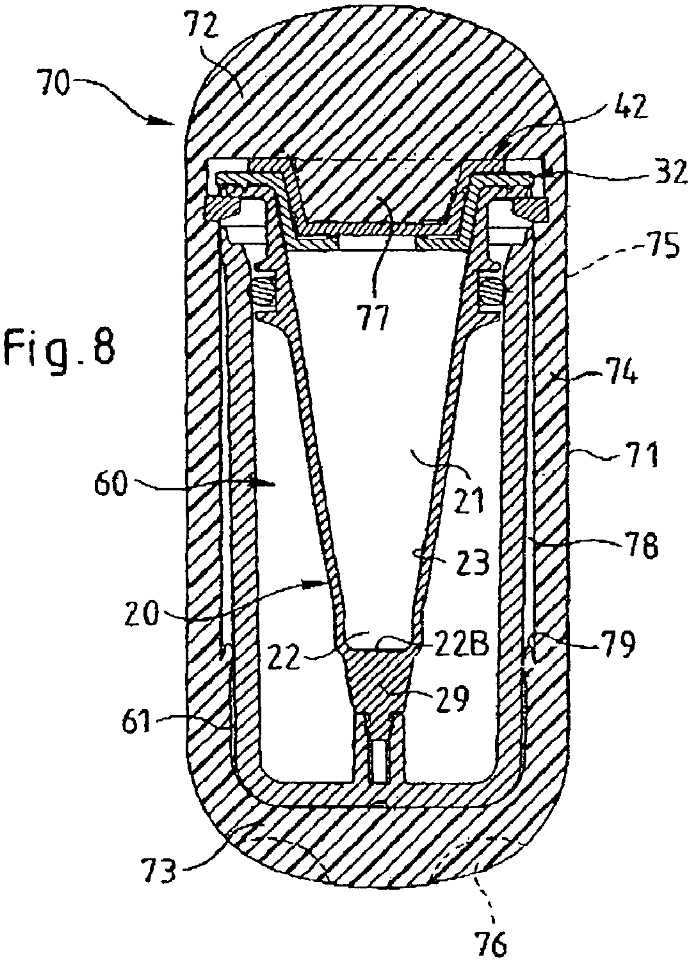
Fig.8
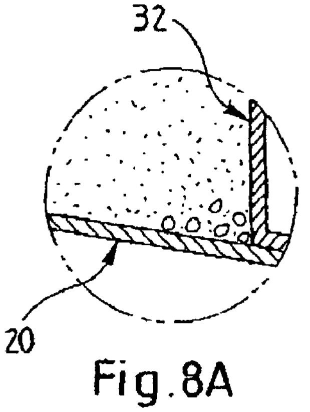
Fig.8A
Fig.9
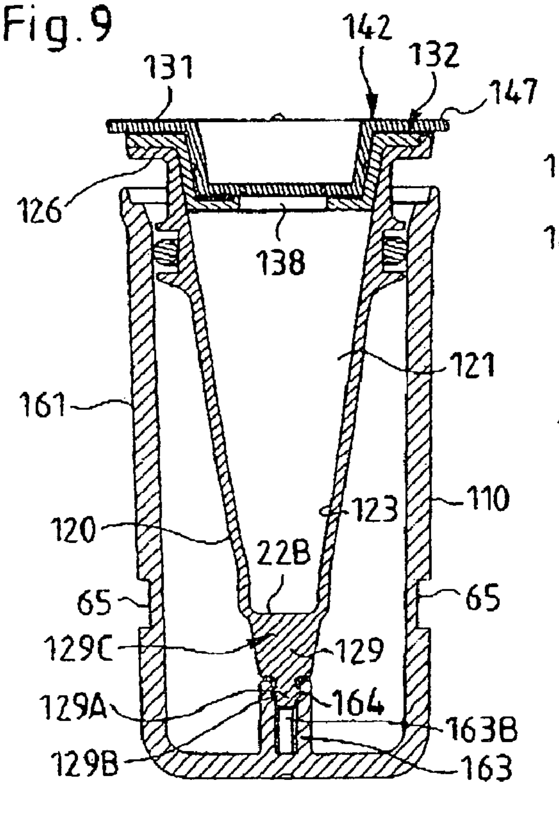
Fig.10
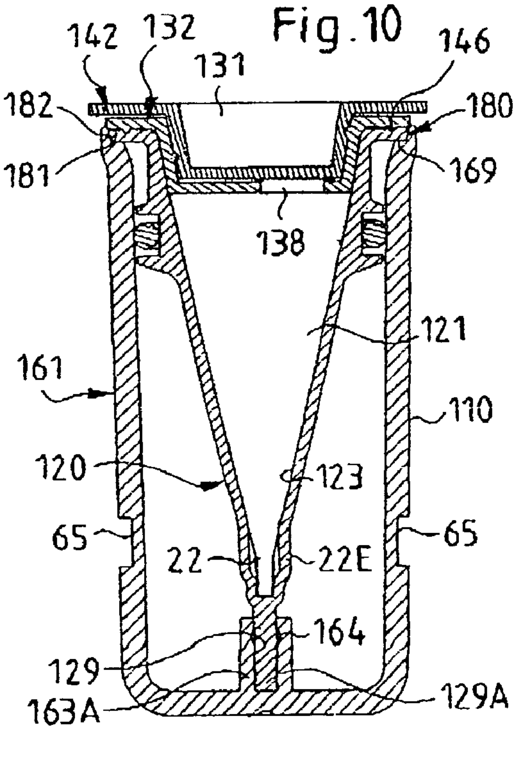

INCUBATION AND/OR STORAGE CONTAINER SYSTEM AND METHOD

BACKGROUND OF THE INVENTION

1. Field of the Invention

The present invention relates to an incubation and/or storage container assembly for gametes and/or at least one embryo and in particular for such a container assembly adapted for use in intravaginal incubation and culture for humans or other mammals.

2. Description of Prior Art

Conventional in-vitro fertilization (IVF) techniques are notoriously complex. They involve aerobic and sterile culture of embryos in Petri dishes at 37° C. in a 5% $CO_2$ enriched atmosphere which requires cumbersome and expensive equipment such as a $CO_2$ incubator operating 24 hours a day during the two or three days required for the fertilization and culture. It also involves delicate manipulations requiring the skills and dexterity of a laboratory biologist.

Intravaginal culture (IVC) has been developed and comprises maturation of gametes, fertilization of oocytes and embryo development in a sealed container filled with a suitable culture medium which is then placed in the vaginal cavity which serves as an incubator. This technology is disclosed in Ranoux U.S. Pat. Nos. 4,902,286 and 5,135,865. It is designed and utilized by assisted procreation specialists in their offices or clinics.

To date, IVC procedures have been performed with a polypropylene Cryotube manufactured by Nunc of Kamptrup, Denmark, which is closed after loading the gametes and sealed in a polyethylene Cryoflex envelope also manufactured by Nunc. IVC procedures using such a container assembly have numerous drawbacks. Many of these drawbacks are overcome with the container assembly disclosed in Ranoux et al U.S. Pat. No. 6,050,935. That patent describes a IVC container assembly comprising a container body and resealable closure means for selectively opening and closing a container body orifice. The container body has a main chamber with a cylindrical sidewall and a microchamber in communication with each other which permits the movement of one or more embryo(s) into and out of the microchamber. The microchamber has sidewalls of optical quality permitting microscopic inspection of embryos. The microchamber also facilitates the retrieval of one or more embryo(s) by means of a catheter without endangering the embryo(s). The container body is equipped with various valve designs which are either bulky or complex construction and/or uneasy to operate. A two-piece capsule of soft flexible material envelopes the container for lodgment in the posterior fornix.

When such a IVC container is taken out of the posterior fornix of the vagina, the outer capsule is removed and the embryos in the microchamber may be inspected under a microscope. One or more embryos is then retrieved from the microchamber by a catheter for transfer to the uterus. This is done while the patient is being prepared for the transfer of the embryo(s). The entire procedure is also designed to be carried out in an obstetrician or other assisted procreation specialist's office with a minimum of equipment.

One of the advantages of the IVC procedure is that fertilization and culture are carried out intravaginally where the atmosphere is naturally $CO_2$ enriched and the amount of oxygen is much lower than of the ambient environment. Both properties are acknowledged as being beneficial, see Alan O. Trounson et al., Handbook of In-vitro Fertilization, CRC Press, Inc., 1993, p. 97 and Misao Fukuda et al., "Unexpected Low Oxygen Tension of Intravaginal Culture", Human Reproduction, vol. 11, no. 6, pp. 1996, 1293-9. Likewise, the temperature is that of the natural environment of the vagina. Once the IVC container is removed from the vagina, it no longer benefits from this ideal natural environment. It is also known that the intravaginally $CO_2$ enriched environment ensures the pH in the container is relatively constant and about 7.3 and that a lower level of $CO_2$ in the container will cause a drop in the pH of the biological medium in which the embryo(s) reside. A relatively small change in the pH (say 0.5) may have drastic consequences over a long period of culture on the embryo(s).

An object of the present invention is to overcome such drawbacks of known IVC containers.

According to one aspect of the invention, a buffer chamber for $CO_2$ enriched atmosphere is provided and cooperable with the vessel containing the biological medium gametes and/or one or more embryo(s) and is in communication with a $CO_2$ permeable wall of the vessel. With such an arrangement, the vessel will remain in a $CO_2$ enriched environment even after it is removed from the $CO_2$ incubation environment or and in particular a vagina. Thereafter, the $CO_2$ enriched air in the buffer chamber will be able to enter the vessel and compensate for any fall in the $CO_2$ level inside the vessel and thereby mediate the pH in the biological medium. Indeed, it has been found if such a buffer chamber is provided on the incubation or storage vessel, the pH level of the biological medium in the vessel will fall only slightly over the period of about one or two hours after the removal of the container assembly from the $CO_2$ enriched environment. Such a small dip in the pH level does not have any significant effect on the embryo(s) in the biological medium.

According to an embodiment, the buffer chamber comprises a shell mounted on the vessel with a $CO_2$ permeable seal disposed between the vessel and the shell to prevent the ingress of liquids or other viscous fluids, in particular vaginal secretions while allowing the inflow of the $CO_2$ enriched air from the surroundings and in the case of intravaginal incubation, from the vagina. In practice, the $CO_2$ inflow rate of the permeable seal will be greater than the inflow rate of $CO_2$ through the permeable wall of the vessel and very much greater than the $CO_2$ outflow rate through the shell wall.

According to another embodiment, the shell is mounted for movement on the vessel between open and closed positions. The shell will be in its open position when the container assembly is introduced into a $CO_2$ enriched air environment, such as a vagina in the case of intravaginal use, and is closed as soon as the container assembly is removed from the $CO_2$ enriched air environment. In such an embodiment, the $CO_2$ enriched air outflow may be virtually nil during the period between the removal of the container assembly from the $CO_2$ enriched environment and the retrieval of the embryos from the vessel for transfer to a recipient, thereby ensuring $CO_2$ equilibration in the biological medium.

In the course of residence in the $CO_2$ enriched intravaginal environment, the level of oxygen in the buffer chamber will reach the favorably depleted $O_2$ level which prevails in the vagina. Thus, after the container assembly is removed, not only is the air inside the buffer chamber advantageously enriched in $CO_2$ but also reduced in $O_2$.

According to an embodiment of the invention, the vessel is provided with a closure device including overlying disc-shaped valve members, each with an orifice, mounted for relative angular movement between an open position for access to the interior of the vessel and a closed position for sealing off access to close the vessel.

According to an embodiment, the peripheral flange of the outer disc-shaped member has a peripheral sidewall radially beyond the peripheral flange of the inner disc-shaped member. One of the peripheral flanges has protrusions selectively cooperable with cutouts in the peripheral sidewall in the other peripheral flange when the valve is in its closed position. Preferably, the peripheral sidewall of the outer disc-shaped member has one or more hooking members for snap fitting axial retention of the outer disc-shaped member on the inner disc-shaped member and/or a peripheral flange of the vessel.

One or both of a pair of opposed sidewalls of the microchamber has an abutment for docking a catheter at the desired location. A portion of the associated recess may define a lens face for viewing one or more embryo(s) in the catheter during or after retrieval from the microchamber.

The inner wall surface of the main chamber of the vessel tapers towards the microchamber. Thus, when the container assembly is received in the posterior fornix, that is in a substantially horizontal position, except when the recipient lays on her side, the inner wall surface slopes to a small zone, where gametes will tend to congregate, thereby enhancing the probability of contact between sperm and oocytes.

These and another objects and advantages of the invention will be brought out in the description of embodiments given by way of example with reference to the accompanying drawings.

BRIEF DESCRIPTION OF DRAWINGS

FIG. 3 is a perspective view, from above, of the fixed inner disc-shaped valve member of the closure device for the vessel.

FIG. 4 is a top plan view of the fixed lower disc of FIG. 3.

FIG. 5 is a perspective view from above of the rotatable upper disc-shaped valve member.

FIG. 6 is a perspective view from below of the rotatable upper disc-shaped valve member.

FIG. 7 is a perspective view from above of the upper part of the container assembly with the closure device in its closed position.

FIG. 8 is a longitudinal sectional view of the container assembly including the outer sleeve for lodging the container assembly in the posterior fornix.

FIG. 8A is an enlarged detail of the vessel wall and lower valve member to illustrate the congregating of oocytes when the container assembly is lodged in the posterior fornix.

FIG. 9 is a longitudinal sectional view of another embodiment of the container assembly in the open position of the buffer chamber, the closure device being in its closed position.

FIG. 10 is a longitudinal sectional view similar to FIG. 9 in the closed position of the buffer chamber.

DETAILED DESCRIPTION OF EMBODIMENTS OF THE INVENTION

The first embodiment of the container assembly 10 for incubating and/or storing gametes and/or one or more embryos is illustrated in FIGS. 1-8. Such a container assembly is suitable for intravaginal incubation or culture (IVC) of human or mammalian embryos, and for use as a storage and transport container for gametes and/or one or more human or other mammalian embryos.

Figure 1:
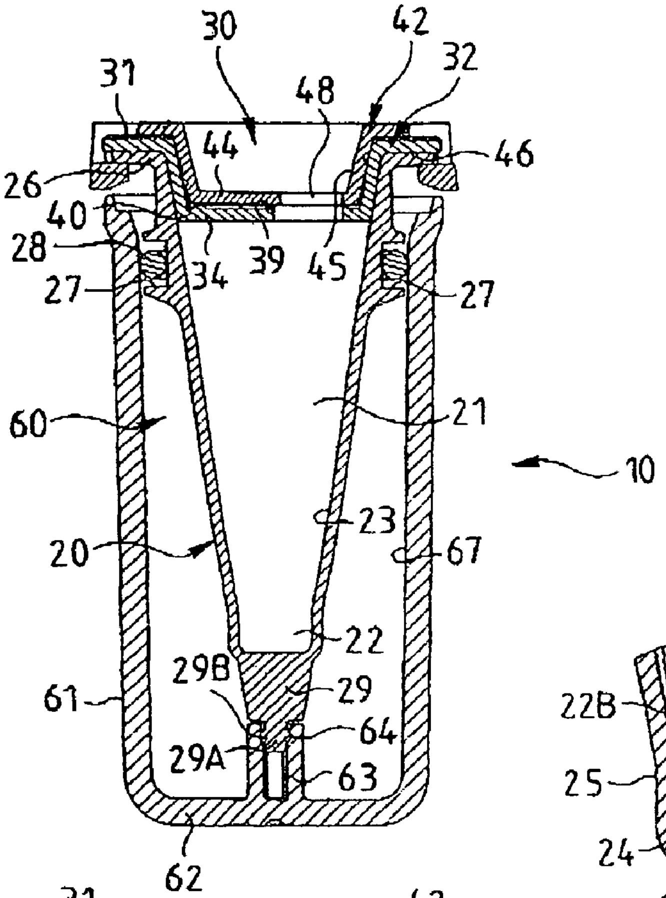
FIG. 1 is a large longitudinal sectional view of a first embodiment of the container assembly with its closure device in an open position.
Figure 2:
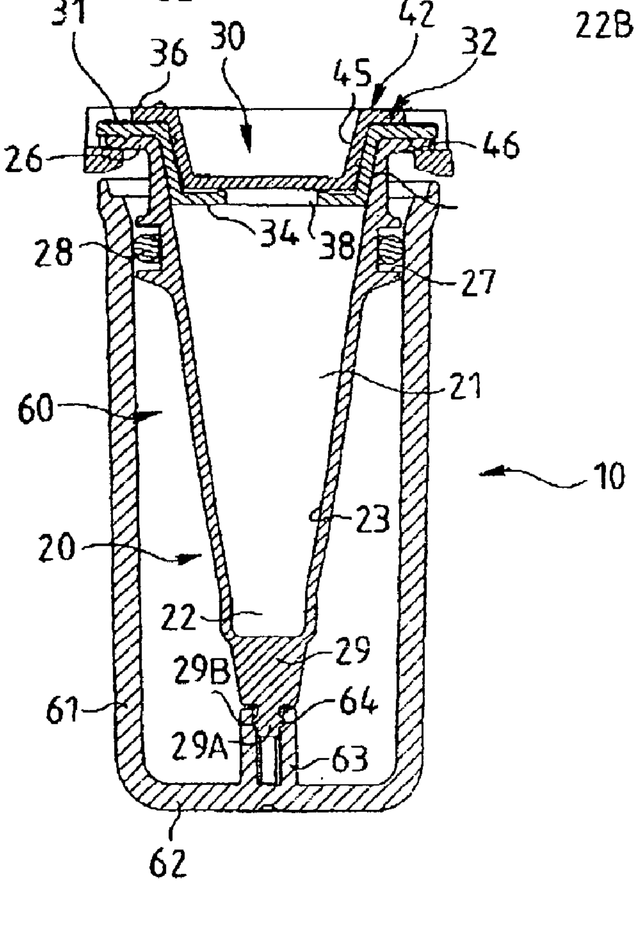
FIG. 2 is a view similar to that of FIG. 1 with the closure device in a closed position.

The terms "upper" and "lower" are used by convention in the specification and claims to refer to relative positions in the container assembly as oriented in FIGS. 1 and 2. It goes without saying that such terms are not intended to be in any way limiting as to orientation or location of the container assembly which in actual practice will vary depending on the stage of the procedure in which it is employed.

The container assembly 10 comprises an inner vessel 20 having a closure device 30 for opening and closing access to the interior of the vessel. The inner vessel 20 is at least partly surrounded and preferably substantially entirely surrounded by a buffer chamber 60 comprising in the illustrated embodiment a shell 61 cooperating with the inner vessel 20.

The inner vessel 20 comprises an upper, main chamber 21 and a lower, microchamber 22 in communication with each other. The inner wall surface 23 of the main chamber tapers towards the generally parallelepipedic microchamber 22. As the upper end of the main chamber in this environment is circular and the lower end is substantially rectangular, the contour of the inner wall surface varies from a circle to a rectangle. The overall shape of the inner wall surface 23 is generally frustoconical with transverse sections that are somewhat flattened oval shapes. The portions of the inner wall surface 23 which lead into wider sidewalls 24 of the microchamber 22 are generally flatter than the portions of inner sidewall which lead into the narrower end walls 25 of the microchamber. At least one of the opposed walls, here sidewalls 24, are of sufficient optical quality to permit inspection under microscope or other magnification instrumentation. In practice, the microchamber 22 and in fact the entire vessel will be made of a material of good optical quality, such as polycarbonate. A suitable polycarbonate is Makrolon RX.2530 45 1118 available from Bayer Chemicals. This polycarbonate has a $CO_2$ permeability of the order of 1000 $cm^3$ 0.001 in/100 $in^2 \times 24$ hr×atm using same units as have been used for Nunc products. The vessel 20 has a peripheral flange 26 extending radially outwardly from the upper end thereof.

The closure device 30 is provided at the open upper end of the vessel body and comprises in a preferred embodiment a valve 31 including two overlying disc-shaped valve members 32, 42. One of the valve members is fixed and the other is mounted for relative angular movement. In practice, the lower valve member 32 is fixed by ultrasonic welding to the upper end of the vessel in practice, the peripheral flange thereof. Each of the valve members comprises a central panel 34, 44 having a port or orifice 38, 48, adapted to be brought into registration in the fully open position of the closure device and out of communication in the fully closed position of the closure device. Each of these orifices 38, 48, is of the same D-shaped contour in the illustrated embodiment. Such a D-shaped contour may limit the access area to permit the entry of only the thinnest of catheters or the largest of pipettes.

Obviously, other contours are possible. The contour edge of one of the orifices 38, 48 and preferably the orifice 38 in the lower valve member 32 has a raised lip or bead 39 for enhanced sealing engagement with the underside of the central panel 44 of the upper valve member. The upper surface of the central panel 44 of the lower valve member has another raised lip or bead 40 spaced from the first raised lip or bead 39, of C-shape as shown, which extends proximate to the outer periphery of the solid portion of central panel 34. The second raised lip or bead 39 ensures that the central panels 34, 44 of the valve members remain parallel to each other to avoid leaking.

Each of the central panels 34, 44 is respectively surrounded by an upwardly or outwardly flaring frustoconical sidewall 35, 45, from the upper end of which extends a radially outwardly extending peripheral flange 36, 46. The respective central panels 34, 44, flaring sidewalls 35, 45 and the peripheral flanges 36, 46 are respectively parallel to each other. One of the mutually contacting surfaces of the sidewalls has a grooved screwthread 47 and the other of the mutually contacting surfaces of the sidewalls has a slider 37 adapted to be received and guided in the grooved screwthread 47. The screwthread 47 and slider 37 have a dual function. One function is to guide angular movement of one disc relative to the other disc and the other function is to separate one disc relative to another disc to break contact between the protruding lip 39 and the central panel 44 of the facing valve member. Other guiding means may be provided instead of the screwthread groove and slider permitting both of these functions. Alternatively, the axial displacement function can be eliminated and a circular groove used in which case there is simply rubbing contact between the raised lips or beads 39, 40 and the facing central panel of the other valve member when the valve member is rotative.

A peripheral sidewall 46A extends downwardly from the peripheral flange 46 of the upper valve member 42 and has a radially inwardly projecting hooking member 49 cooperable with the undersurface of at least one of the peripheral flanges of the vessel and fixed valve member and as shown under the undersurface of peripheral flange 26 of the vessel 20. The peripheral, flange 46 and the adjoining peripheral sidewall 46A have a plurality of spaced cutouts 50, a first portion 50A of each cutout having radially inwardly flaring sides 50B being located in the peripheral flange and a second portion 50C extending downwardly along the peripheral sidewall 46A and defined by leading and lagging parallel edges 50D, 50E generally in alignment with the respective hooking members 49.

The outer peripheral edge 36A of the peripheral flange 36 of the lower valve member has one or more protrusions 36B defined by a generally radial edge and generally circumferential or tangent edge and two such protrusions 36B diametrically opposed and mirror images of each other, as shown. The protrusions are adapted to clickingly clear the respective leading edges of the second portions 50D of the cutouts 50 to provide an audible signal that the closed position of the closure member has been reached (see FIG. 7).

The lower and upper disc-shaped valve members 32, 42, may be assembled in the following manner. The upper valve member 42 is positioned on top of the lower valve member 32 previously ultrasonically welded to the vessel, and pressed downwardly. The edge 36A of the peripheral flange 36 will ride along and clear the oblique undersurfaces 49A of the hooking members 49 and snap into the space 49C between the upper end surface of the hooking member 49 and the underside of the central panel 44B of the upper valve member 42. The outer diameter of the peripheral flange 36 of the lower valve member and the peripheral flange 26 of the vessel is slightly greater than the diametrical distance between the radially inner ends 49B of the hooking members 49 thereby preventing the escape of the outer valve member off of the peripheral flange of the vessel.

The lower valve member 32 may be made of the same polycarbonate used for the vessel or some other material compatible for ultrasonic welding with the peripheral flange of the vessel. The upper valve member is preferably made of a softer material than the material used for the lower valve member in order to enhance the sealing action of the contour lip or bead. For example, a polypropylene available from Huntsman Corp. under reference 13G9A is suitable.

The outer surface of the vessel body has a radially outwardly opening annular groove 27 for accommodating a sealing member 28 which may be a O-ring, as illustrated in FIGS. 1 and 2. When the vessel is received in the shell 61, the sealing member 28 is in sealing engagement with the intermediate, bight portion of the groove 27 and the inner wall surface 67 of the shell 61 in alignment therewith. The sealing member in the illustrated embodiment has various features, the most important of which is its high $CO_2$ permeability and $CO_2$ flow rates permitting the inflow of $CO_2$ enriched air from a surrounding $CO_2$ enriched environment. The $CO_2$ inflow rate should enable the $CO_2$ level in the buffer chamber to reach the level in the surrounding $CO_2$ environment in less than about eight hours and preferably in less than about three hours. The flow rate should not be too high so as to cause a significant outflow of the $CO_2$ enriched gas from the buffer chamber in less than two hours. Another advantageous feature of the sealing member is its permeability to $O_2$ to enable the depleted levels of $O_2$ in the $CO_2$ enriched environment to replace the normal level of $O_2$ in the ambient air after the container assembly is placed in the CO2 enriched and $O_2$ lean environment. In practice, the sealing member will be air permeable and therefore allows the in- and outflow of all gases in the ambient air, especially $N_2$, $CO_2$ and $O_2$. Another advantageous feature of the sealing member is to define a barrier to liquids or viscous substances and in particular vaginal secretions when the container assembly is intended for intravaginal use. Another advantageous feature of the sealing member is to define a barrier against the entry of bacteria and even viruses present in a vagina when the container assembly is to be used intravaginally. Such a sealing member effective against the ingress of vaginal secretions, bacteria and viruses will prevent their entry into the buffer chamber and avoid possible contamination of the contents of the vessel via the vessel walls. A suitable material having all foregoing features is a medical grade silicone which has a very high permeability of the order of 300,000 $cm^3$×0.001 in/100 $in^2$×24 hr×atm. Such an example is, however, not intended to be limiting. The $CO_2$ permeability of the seal may be very much less than that of medical grade silicone and even low as about 7.6 $cm^3$×0.001 in/100 $in^2$×24 hr×atm in the case of a Nylon 66 gasket. Whatever the seal material is selected, it should enable equilibration between $CO_2$ level in the $CO_2$ enriched environment of the vagina or other incubator and that of the buffer chamber in less than about eight hours and preferably in about three hours.

The shell is made of a material having good clarity for inspection of the contents in the microchamber through the wall of the shell. To this end, it preferably has diametrically opposed planar zones 65 of optical quality adapted to be in alignment with the sidewalls of the microchamber. A suitable material for the shell is PETG such as Eastar MN058 available from Eastman Chemical Co. having a permeability of about 80 $cm^3$×0.001 in/100 $in^2$×24 hr×atm. Alternatively, polycarbonate may be used for the shell wall. As polycarbonate is also used for the vessel wall, the thickness of the shell wall should be at least about twice the thickness of the vessel wall to ensure that the $CO_2$ flow rate through the vessel wall will be substantially greater than the $CO_2$ flow rate through the shell. The shell may alternatively be made of a material having a substantially nil $CO_2$ permeability such as, for example, glass having suitable mechanical properties. When a shell of nil or very low permeability is employed, obviously essentially all $CO_2$ and/or $O_2$ flow will be through the seal between the vessel wall and the shell wall.

According to an embodiment, the $CO_2$ permeability of the seal is selected to be, say, one or two orders of magnitude greater than the permeability of the vessel wall and at least two orders of magnitude greater than the $CO_2$ permeability of the shell wall. An example of such an embodiment is a silicone seal having a $CO_2$ permeability of the order of 300,000 $cm^3$×0.001 in/100 $in^2$×24 hr×atm, a vessel made of Makrolon polycarbonate having a $CO_2$ permeability of the order of 1,000 $cm^3$×0.001 in/100 $in^2$×24 hr×atm and a shell made of Eastar PETG having a permeability of about 80 $cm^3$×0.001 in/100 $in^2$×24 hr×atm.

According to another embodiment, the respective materials are selected so that the $CO^2$ permeability of the seal is between about 7.6 $cm^3$×0.001 in/100 $in^2$×24 hr×atm (corresponding to Nylon 66) and about 300,000 $cm^3$×0.001 in/100 $in^2$×24 hr×atm (corresponding to medical grade silicone), the $CO_2$ permeability of the vessel is between 20 $cm^3$×0.001 in/100 $in^2$×24 hr×atm (corresponding to the permeability of PVC) and about 300,000 $cm^3$×0.001 in/100 $in^2$×24 hr×atm, and the shell has a $CO_2$ permeability between about 0 (corresponding to glass) and 80 $cm^3$×0.001 in/100 $in^2$×24 hr×atm (corresponding to PETG).

The vessel and/or the seal material may be also chosen in order to slightly delay the entry of the $CO_2$ enriched gas into the vessel to counter the initial generation of acidic metabolic products during which the $CO_2$ in the vessel which should be allowed to permeate through the vessel wall into the buffer chamber maintaining the desired equilibration level, while thereafter allowing the $CO_2$ enriched environment to flow into the vessel in order to maintain a pH of about 7.4 once acidic metabolic products cease to be produced.

When the container assembly is not intended for intravaginal use, there may be no need to prevent the ingress of liquids or other viscous fluids.

Sealing member configurations other than O-rings may be useful and in particular annular gaskets having a rectangular cross section and therefore the same gas flow rate through the entire radial extent of the cross section.

In practice, the sealing member will have an inner diameter in its rest configuration which is slightly less than the corresponding outer diameter of the complementary bight portion of the groove and an outer diameter which is slightly greater than the inner surface of the shell in contact to cause elastic deformation and thereby ensure a snug fit and satisfactory tightness.

The lower end 29 of the vessel 20 that is the trapezoidal shaped portion (as shown) of the vessel situated below the microchamber 22 will in practice be solid and not hollow. The lower end 29 of the vessel has a locating member 29A cooperable with a complementary locating member 63 of hollow cylindrical configuration and upstanding from the bottom 62 of the shell 61 in the illustrated embodiment. The locating member 29A has at least one protruding bead or boss 29B which is cooperable with a complementary groove or recess 64, so as to define a stable position of the vessel when the vessel is fully inserted into the buffer chamber. Alternatively, or in combination with the aforesaid locating members 29A, 63, the abutting surfaces of the top edge of the locating member 63 and the downwardly facing annular shoulder of the lower end 29 may define the fully inserted position of the vessel relative to the shell 61.

Guiding members (not illustrated) may be provided to guide the movement of the vessel to ensure the locating member 29A at the lower end 29 is correctly engaged into the complementary locating member 63. Such guiding members may for example comprise two or more fin-like elements integral with the outer wall of the vessel or the inner wall of the shell and cooperable with the other of the outer wall of the vessel or the inner wall of the shell.

Such a container assembly as illustrated in FIGS. 1 and 2 may be filled with a suitable biological medium, such as INRA Menoza B2 medium available from Laboratoire CCD in Paris, whereupon the gametes, namely sperm and oocytes may be introduced in that order through the orifices at least partly in registry to enable the insertion of a catheter or pipette into the main chamber of the vessel while minimizing the size of the open access area. Thereafter, the catheter or pipette is taken out and the closure device is immediately closed, sealing off the interior of the vessel from the environment. The shell 61 is preferably positioned on the vessel prior to filling and loading of gametes. It is then suitable for incubation at about 37° C. in a conventional incubator with a $CO_2$ enriched environment in which case the main function of the sealing member will be to ensure the build-up of $CO_2$ enriched environment in the buffer chamber and which after removal of the container assembly from the incubator will serve as a reservoir for $CO_2$ enriched air to mediate the aqueous pH level inside the vessel.

This assembly, however, is especially designed for use in intravaginal incubation. To this end, it will be preferably enveloped in a container sleeve or carrier 70 for facilitating intravaginal residence in the posterior fornix. The container sleeve 70 is made of a soft smooth elastic biocompatible material such as a silicone. In the illustrated embodiment, the sleeve 70 is of one-piece construction with an apertured sidewall 71 extending between opposed rounded ends 72, 73 suitable for cooperation with the vaginal vault. The lower rounded end 73 has on its outside surface a plurality of circumferentially spaced dimples 76 for facilitating the removal of the entire container assembly by means of forceps cooperating with dimples. The upper portion of the lower rounded end converges inwardly (in the rest condition) in order to enhance the elastic engagement with the bottom end of the shell 61. The sidewall 71 comprises in practice a plurality, here two, circumferentially spaced longitudinal straps 74 defining apertures 75 therebetween. At least one of the apertures 75 is suitable for the introduction of the container assembly into the internal space 76 of the container sleeve 70. In the embodiment illustrated, the upper rounded end 72 is larger than the lower rounded end 73 and comprises a plug portion 77 complementary in shape and adapted to be received in the recess defined by the sidewalls 45 and central panel 44 of the upper valve member 42. One or both of the straps 74 may have a radially inwardly protruding lip 79 cooperable with the outer edge of the lower valve member and/or peripheral flange 26 of the vessel. Similarly, the inner surface of the bottom rounded end 73 is generally complementary to the bottom wall of the shell 61. In the relaxed position of the container sleeve 70, that is before it is fitted on the container assembly 10, the distance between the inner face of the plug portion 76 of the upper rounded end and the inner or the lower face of the lower rounded end of the container sleeve is less than the distance between the outer surface of the bottom wall 62 of the shell and the outer surface of the central panel 44 of the upper valve member, so that an axial biasing force is exerted by the container sleeve 70 in order to urge the inner and outer valve members into contact and define a second tier sealing between the interior of the vessel and the surrounding environment. In practice, the total length of the entire container assembly with the container sleeve will be about 5-6 cm for a woman or about 10-15 cm for a cow. The container sleeve may be made of a medical grade thermoplastic elastomer, such as AES Santoprene 8211-35 W237 having a hardness of 35 Shore A and good cushioning properties.

After the container assembly 10 is closed with the sleeve fitted thereon, it may be introduced into the vaginal vault and positioned in the posterior fornix for 48-72 hours according to current procedure prior to introduction into the vaginal vault, the container assembly may undergo pre-incubating at 37° C. with or without the sleeve for less than two hours, safely in a conventional incubator without a $CO_2$ enriched environment and for the whole incubation period in a $CO_2$ enriched environment.

When the container assembly is lodged in the posterior fornix, the longitudinal axis of the vessel will be generally horizontal. As the inner wall surface slopes away from the microchamber and towards the closure member, gametes and in particular oocytes will tend to congregate in the vicinity of the zone where the undersurface of the central panel of the lower valve member meets the inner wall surface of the vessel, as illustrated in FIG. 8A, as this will be the lowest level of any part of the combined main and micro chambers when the container assembly is lodged in the posterior fornix. This arrangement is advantageous for enhancing the potential of contact between sperm and oocytes. In a variant (not illustrated), the inner wall surface of the vessel may have its largest dimension between the upper and lower ends of the main chamber, for example by adopting a double frustoconical the sidewall surface joined at their large bases. This variant arrangement, as well as other possible arrangements may assist the congregating of the gametes in a limited zone of the main chamber to enhance the potential for fertilization of oocytes.

After intravaginal residence, the container assembly is removed. For this purpose, a monofilament string (not shown) of biocompatible material may be attached to or integrally formed with one of the ends or the straps of the container sleeve.

The container assembly is then taken out of the container sleeve. The contents of the microchamber where the embryo (s) will settle by gravity (in the FIG. 1 position) may then be inspected through one of the opposed sidewalls 24 of the microchamber in a recumbant or upright position. The shell 61 has corresponding aligned parallel surfaces 65 of optical quality aligned with the opposed sidewalls 24, in order not to interfere with the inspection of the embryo(s) which will normally be carried out with a laboratory microscope.

Figure 1A:
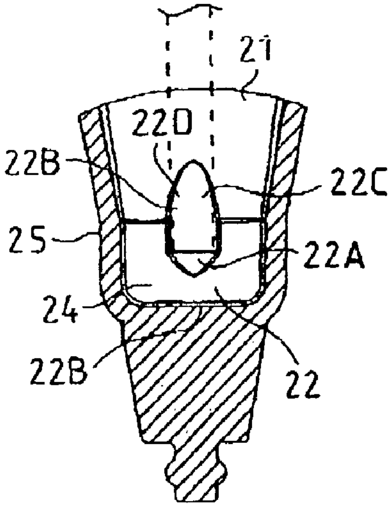
FIG. 1A is an enlarged longitudinal sectional view of the lower end of the vessel of the container assembly to illustrate the catheter docking abutment in the vessel wall.

Once the desired embryo(s) have been selected, an implantation catheter such as Frydman or Wallace catheter is introduced after slightly opening the closure device by turning the upper valve member. The catheter is then snaked through the main chamber to a location proximate the junction of the main chamber and the microchamber which is equipped with an abutment 22A in a wall of the microchamber, and in practice a pair of abutments in the opposed sidewalls for docking the end of the catheter at a sufficient height above the floor 22B of the microchamber to prevent the catheter from coming into direct contact and thereby possibly crushing or otherwise injuring the embryo(s) in the microchamber (see FIG. 1A) As illustrated, the docking abutment(s) is located midway across the opposed sidewalls 24 of the microchamber so that the microchamber is aspirated to either side. Alternatively, the docking abutment may be located to one side or the other of the microchamber as disclosed in Ranoux et al. U.S. Pat. No. 6,050,935. The desired embryo(s) may then be aspirated into the catheter and inspected as they are drawn upwardly. Indeed, for that purpose, a portion of the recess 22C defining the abutment 22A also defines an interior lens face 22D. The outer surface of the vessel proximate to the junction of the main chamber and microchamber has an exterior lens face 22 E in optical alignment with the interior lens face 22D. The lens on one or both sides of the microchamber may be used for viewing the one or more embryo(s) in the catheter during or after the retrieval from the microchamber.

The embryo(s) may then be implanted in accordance with current practice.

Another embodiment is illustrated in FIGS. 9 and 10. This second embodiment is suitable for the same purposes as the first embodiment and is of particular interest when the container assembly with its gamete(s) and/or embryo(s) are to be stored for a prolonged period, for example to enable the contents to be shipped prior to implantation. Indeed, in this embodiment, a closure seal is provided between the vessel and the shell and in series with the $CO_2$ permeable sealing member to prevent the egress of the $CO_2$ and/or $O_2$ out of and/or the ingress of gas into the buffer chamber when the container assembly is removed from the vagina or a $CO_2$ enriched incubator.

Features of the second embodiment corresponding to features of the first embodiment are identified by the same references augmented by “100” and will not again be described.

In the second embodiment, the upper or outer disc-shaped valve member terminates in the peripheral flange 146 which comprises opposed pairs of radial projections 147 alternating with and separated by concave zones. The radial projections 147 alternating and separated by and/or the concave zones facilitate the grasping of the upper disc-shaped valve member for facilitating turning between open and closed positions of the valve. As in the first embodiment, a slider on the upper or outer valve member 142 may ride along the screwthread groove in the lower valve member between a position in which the orifices 138, 148 are out of communication with each other and the solid portions of the central panels 134, 144 overlying each other and are in mating contact with the contour edges of the orifices.

Instead of a single position of the vessel relative to the shell disclosed in the first embodiment, the vessel 120 and the shell 161 have two stable positions, namely an open position or condition for use when the container assembly is placed in a $CO_2$ enriched environment for incubating the contents and a closed position or condition for sealing the buffer chamber and preventing the escape of the $CO_2$ enriched and $O_2$ depleted contents or the entry of ambient air from the surroundings after the container assembly has been removed from the incubating environment.

The first position or condition is illustrated in FIG. 9 and the second position or condition illustrated in FIG. 10. The FIG. 9 position corresponds substantially to the FIG. 2 position of the first embodiment. The lower end portion 129 has a downwardly protruding locating member 129A selectively cooperable with a complementary corresponding locating member 163 of hollow cylindrical configuration, as illustrated and upstanding from the bottom wall 162 of the shell 161. The locating member 129A has a pair of axially spaced protruding beads or bosses 129B, 129C, selectively cooperable with corresponding complementary groove or recess 164. The protruding beads 129B, 129C are located approximately at 90° from each other relative to the general longitudinal axis of the vessel 120. Thus, in the first position, the protruding beads or bosses 129B come into engagement with the groove or recess 164 and in the second position, the protruding beads or bosses 129C come into engagement with the complementary groove or recess 164. To change positions, the vessel 120 must be rotated 90° and depressed (or raised) until it reaches the other position.

In the lower position, a closure seal 180 is defined by the annular notch 169 at the upper end of the shell 161 which is cooperable with a peripheral portion 181 of the undersurface of the peripheral flange 126 of the vessel and the free edge 182 of the peripheral flange of the vessel and possibly the free edge of the peripheral flange of the lower valve member 132. The closure seal 180 is essentially defined by the contact between the notch and the portions of the peripheral flange of the vessel. In accordance with a variant, not illustrated, an additional sealing member or gasket may be provided either at the upper end of the shell or at the peripheral flange of the vessel and/or lower valve member. Such an additional sealing member or gasket will be of very low gas permeability to prevent the escape of the atmosphere contained in the buffer chamber or the entry of the ambient atmosphere into the buffer chamber. Such an embodiment is therefore suitable for prolonged storage of many hours or even days. According to a variant (not illustrated) the $CO_2$ permeable seal is readily replaceable with another $CO_2$ permeable seal having a different $CO_2$ inflow rate from that of the first-mentioned $CO_2$ permeable seal.

Figure 11:
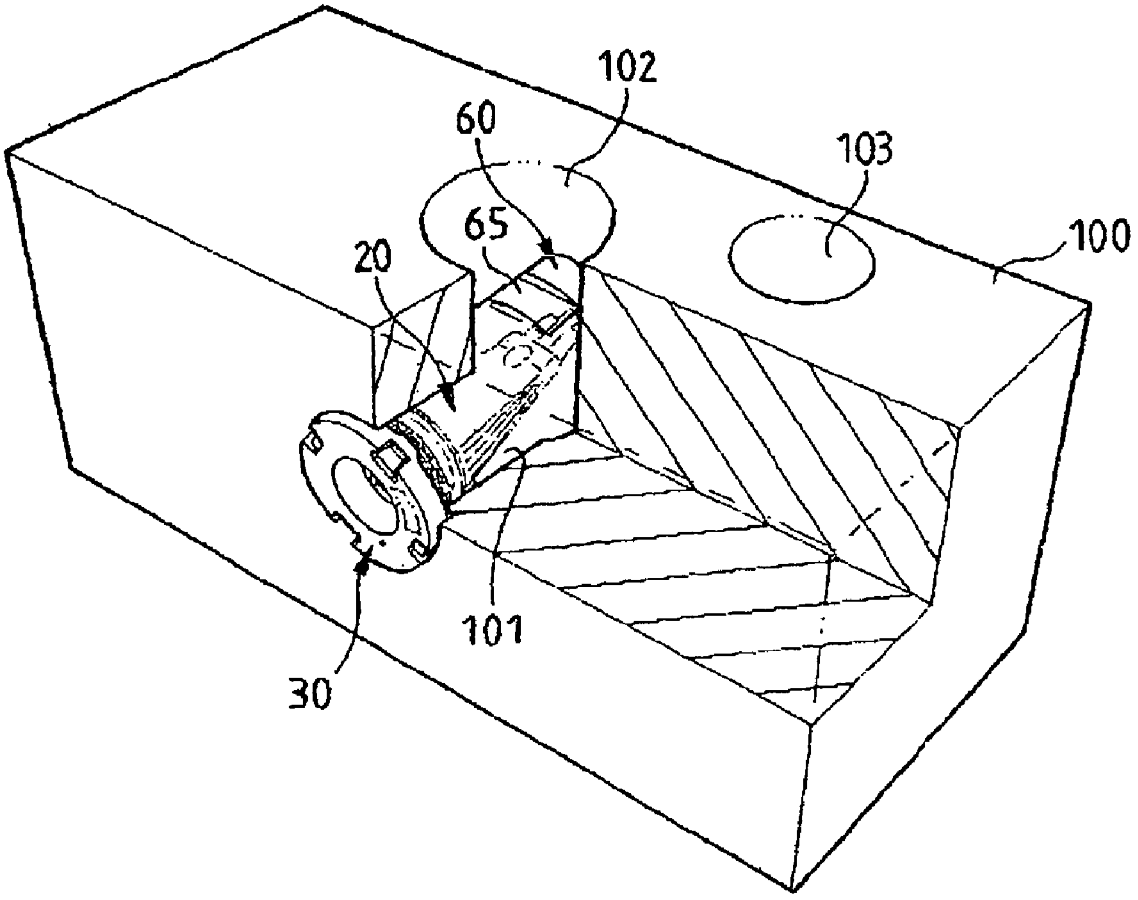
FIG. 11 is a perspective view partially cut away of the container assembly received in a holding block for inspecting the embryo(s).

For such a purpose, the container assembly should be loaded into a pre-heated isothermal holding block for maintaining the contents of the vessel substantially constant at about 37° C. An embodiment of such a holding block 100 is illustrated in FIG. 11. The holding block is preferably made of steel, but alternatively may be made of any material having a relatively high level of thermal inertia. As illustrated, the block is parallepipedic with a lateral bore 101 extending from one side of the block to a point beyond the middle thereof where it is in communication with a vertical bore 102. The vertical bore 102 extends from the top to the bottom of the block, the lower portion of the bore being of smaller cross section than the upper portion of the bore.

Before the holding block is be to used, it is heated to the desired temperature of about 37° C. When the connecting assembly is fully inserted in the lateral bore, the microchamber and the corresponding surface 65 of optical quality on the shell 61 will be aligned with the vertical bore 102 for viewing the embryo(s) or other contents of the microchamber with a microscope. The part of the container assembly and in particular the microchamber located at the intersection of the lateral and vertical bores is lit from below through a light shaft defined by the lower portion of the vertical bore 102.

Alternatively, the container assembly without the shell may be introduced into the lateral bore for viewing the contents of the microchamber in which case there is no need for the surface(s) 65 of optical quality. According to another embodiment (not shown), the block is equipped with a heating element for maintaining the temperature of the block substantially constant at about 37° C. and may be of particular interest for use when the container is to be shipped or transported to another location for inspection of the embryo(s). The top surface of the block also has one or more vertical aligned bores 103 for receiving in a substantial vertical position one or more container assemblies prior to inspection or smaller tubes for containing sperm or oocytes.

It would be appreciated that these and other modifications and variants may be adopted without departing from the spirit and scope of the invention defined by the appended claims.

The invention claimed is:

1. A container assembly comprising (i) a vessel for containing a biological medium as well as gametes and/or one or more embryo(s), the vessel having a wall which confines the biological medium, gametes and/or embryo(s) inside the vessel, said vessel wall including a $CO_2$ permeable wall; (ii) a closure device for selective access to the interior of the vessel, and (iii) a buffer gas chamber for containing a $CO_2$ enriched atmosphere and including a shell cooperable with said vessel, the buffer gas chamber including the shell being disposed around the vessel and the $CO_2$ enriched atmosphere being in communication with the $CO_2$ permeable wall for supplying $CO_2$ enriched atmosphere to the contents of the vessel such that an inner surface of the vessel wall is in contact with liquid contents of the vessel and an outer surface of the vessel wall is in contact with CO2 enriched gas of the buffer gas chamber.

2. The container assembly according to claim 1, wherein the buffer chamber has an open condition for communication with an external $CO_2$ enriched environment and a closed condition for closing off the chamber from the external $CO_2$ enriched environment.

3. The container assembly according to claim 1, wherein substantially the entire vessel wall is $CO_2$ permeable.

4. The container assembly according to claim 1, wherein the buffer chamber has a lower $CO_2$ outflow rate than the $CO_2$ inflow rate of the vessel.

5. The container assembly according to claim 1 wherein the vessel and the closure device together define an incubation chamber, the closure device comprising lower and upper disc-shaped members having respective registrable orifices for accessing the interior of the vessel, the lower disc-shaped member being fixed relative to the vessel, at least one of the vessel and the lower disc-shaped member having a peripheral flange, the upper disc-shaped member being mounted for rotation on the lower disc-shaped member, the upper disc-shaped member having one or more peripheral hooks for clipping the upper disc on the peripheral flange for restraining the upper disc-shaped member separating from the vessel in any relative angular position, the closure device having an open position in which the orifices are in registration and a closed position in which the orifices are out of registration and the upper disc-shaped member is in sealing engagement over the orifice of the lower disc-shaped member.

6. The container assembly according to claim 1, wherein the vessel has a peripheral flange, and the vessel and the closure device together define an incubation chamber, the closure device comprising lower and upper disc-shaped members with respective registrable orifices for accessing the interior of the vessel, the lower disc-shaped member being fixed relative to the vessel, at least one of the vessel and the lower disc-shaped member having a peripheral flange, the upper disc-shaped member being mounted for rotation on the lower disc-shaped member between a position in which the orifices are in and out of registration, the upper disc-shaped member having a peripheral skirt including cutouts at circumferentially spaced locations, the peripheral flange having at least one of the radial protrusions audibly clearing an edge of at least one of the cutouts, and the closure device having an open position when the orifices are in registration and closed position in which the orifices are out of registration and the upper disc-shaped member is in sealing engagement over the orifice of the lower disc-shaped member, whereby the protrusion audibly clearing said edge of the one of the cutouts as the closure device reaches the closed position.

7. The container assembly according to claim 1, wherein the closure device comprises a valve.

8. The container assembly according to claim 1 in combination with a preheated holding block having at least one bore for holding at least one said vessel.

9. The combination according to claim 8, wherein the holding block comprises a heating element for maintaining the temperature of the block substantially constant at about 37° C.

10. The combination according to claim 8, wherein the preheated holding block has a lateral bore for receiving the vessel and a vertical bore in communication with the lateral bore, the vessel having a microchamber with opposed walls of suitable quality for viewing the contents of the microchamber under magnification, the microchamber being positioned in alignment with the vertical bore so that the contents of the microchamber can be viewed under magnification.

11. The container assembly according to claim 1 in combination with a preheated holding block having at least one bore for holding at least one said vessel together with the associated buffer chamber.

12. The combination according to claim 11, wherein the vessel together with the buffer chamber are adapted to be received in the lateral bore, and wherein the shell defining the buffer chamber has a surface of optical quality in alignment with the microchamber of the vessel for viewing the contents of the microchamber under magnification.

13. A container assembly comprising: (i) a vessel for containing a biological medium as well as gametes and/or one or more embryo(s), the vessel having a $CO_2$ permeable wall which confines the biological medium, gametes and/or embryo(s) inside the vessel; said vessel wall including a $CO_2$ permeable wall; (ii) a closure device for selective access to the interior of the vessel, and (iii) a buffer gas chamber for containing a $CO_2$ enriched atmosphere and including a shell cooperable with said vessel, the buffer gas chamber being disposed around the vessel and the $CO_2$ enriched atmosphere being in communication with the $CO_2$ permeable wall, wherein the shell is mounted relative to the vessel for movement between an open position for communication with an external $CO_2$ enriched environment and a closed position for closing off communication between the buffer chamber and the external $CO_2$ environment.

14. The container assembly according to claim 13, wherein the closure device comprises a valve.

15. A container assembly comprising (i) a vessel for containing a biological medium as well as gametes and/or one or more embryo(s), the vessel having a $CO_2$ permeable wall which confines the biological medium, gametes and/or embryo(s) inside the vessel, said vessel wall including a $CO_2$ permeable wall; (ii) a closure device for selective access to the interior of the vessel, and (iii) a buffer gas chamber for containing a $CO_2$ enriched atmosphere and including a shell cooperable with said vessel, the buffer gas chamber being disposed around the vessel so that the $CO_2$ enriched atmosphere is in communication with the $CO_2$ permeable wall, wherein the vessel comprises a main chamber and a microchamber for communication of the biological medium, gametes and/or one or more embryo(s) therebetween, the microchamber and at least part of the main chamber being surrounded by the buffer chamber and the $CO_2$ permeable wall including a wall portion defining the microchamber.

16. The container assembly according to claim 15, wherein the closure device comprises a valve.

17. A container assembly comprising (i) a vessel for containing a biological medium, gametes and/or one or more embryo(s), the vessel having a wall which confines the biological medium, gametes and/or embryo(s) inside the vessel, (ii) a closure device for selective access to the interior of the vessel, said vessel wall including a $CO_2$ permeable wall; and (iii) a buffer gas chamber for containing a $CO_2$ enriched atmosphere and including a shell cooperable with said vessel, the buffer gas chamber being disposed around the vessel and the $CO_2$ enriched atmosphere being retained inside the buffer gas chamber, the buffer gas chamber being in communication with the $CO_2$ permeable wall for $CO_2$ equilibration in the vessel after the container assembly is out of communication with a $CO_2$ enriched environment, wherein the wall vessel is made of a plastic material which confines liquid contents of the vessel while the $CO_2$ permeable wall allows ingress of $CO_2$ enriched atmosphere from the buffer chamber.

18. The container assembly according to claim 17, wherein the buffer chamber bas an open condition for communication with the $CO_2$ enriched environment and a closed condition for closing off the buffer chamber surroundings after when the container assembly is out of communication with the $CO_2$ enriched environment.

19. The container assembly according to claim 17, wherein the vessel comprises a main chamber and a microchamber both containing the biological medium for flow therebetween, main chamber and microchamber being substantially surrounded by the buffer chamber and the $CO_2$ permeable wall including a wall defining the main chamber and the microchamber.

20. The container assembly according to claim 17, wherein the $CO_2$ gas permeable wall defines substantially the entire wall of the vessel.

21. The container assembly according to claim 17, wherein the buffer chamber has a $CO_2$ outflow rate substantially lower than the $CO_2$ inflow rate of the vessel.

22. The container assembly according to claim 17, wherein the closure device comprises a valve including disc-shaped members in overlying relationship mounted for relative angular movement.

23. The container assembly according to claim 22, wherein an inner one of the disc-shaped members is fixed relative to the vessel and an outer one of the disc-shaped members is mounted for angular movement.

24. The container assembly according to claim 23, wherein each of the disc-shaped members has an orifice in a central panel for introducing a catheter or pipette for gametes and/or one or more embryo(s), an upstanding sidewall around the central panel and a peripheral flange extending radially outwardly from the sidewall.

25. The container assembly according to claim 24, wherein an upper part of the vessel has a frustoconical sidewall and a peripheral flange extending outwardly therefrom, the sidewalls of the disc-shaped members being frustoconical and having the same cone angle as the frustoconical sidewall of the upper part of the vessel, and the peripheral flanges of disc-shaped members extending parallel to the peripheral flange of the vessel.

26. The container assembly according to claim 22, wherein one of the disc-shaped members of the closure device has a protruding lip along an edge defining an orifice therein, the lip facing the other of the disc-shaped members of the valve and sealingly engageable therewith.

27. The container assembly according to claim 26, wherein said one of the disc-shaped members has a raised portion of substantially the same height of the protruding lip and spaced therefrom for maintaining the central panels parallel to each other.

28. The culture container assembly according to claim 22, wherein a lower one of the disc-shaped members of the valve has a protruding lip along an edge defining an orifice therein, the lip facing the upper one of the disc-shaped members of the valve and sealingly engageable therewith.

29. The container assembly according to claim 24, wherein the peripheral flange of upper one of the disc-shaped members has a peripheral sidewall radially outwardly beyond the peripheral flange of a lower one of the disc-shaped members the peripheral flange of the lower disc-shaped members having protrusions selectively cooperable with cutouts in the peripheral sidewall in a closed position of the closure device.

30. The container assembly according to claim 24, wherein the peripheral sidewall of the upper disc-shaped member has one or more hooking members for snap-fitting axial retention of the upper disc-shaped member on the lower disc-shaped member.

31. The container assembly according to claim 17, wherein the vessel comprises a main chamber and a microchamber for the flow of the biological medium therebetween and the movement of gametes and/or one or more embryo(s) therebetween, the inner wall surface of the main chamber member tapering from an end fitted with the closure device, towards the microchamber.

32. The container according to claim 17, wherein the buffer chamber comprises a shell having a marking surface on an external wall for patient identification.

33. The container assembly according to claim 17, wherein the vessel and closure device define an intravaginal container for intravaginal incubation, and further comprising a container sleeve with opposed rounded ends suitable for cooperation with a vaginal vault, the rounded ends having inner faces cooperable with opposed ends of the container, and an elastic sidewall connecting the rounded ends and urging the inner faces towards each other when the container is received in the sleeve.

34. The intravaginal incubation container assembly according to claim 33, wherein the elastic sidewall has one or more openings for introduction and removal of the intravaginal container.

35. The intravaginal incubation container assembly according to claim 33, wherein an inner face of one of the sleeve ends has a plug engageable in and mating with a central recess defined by the closure device for urging elements of a closure device towards each store.

36. The container assembly according to claim 19, wherein the microchamber has opposed walls of suitable quality for viewing the contents of the microchamber under magnification, an abutment being provided on an inner surface of one or both of the opposed walls for docking a catheter, substantially at the middle of the opposed walls.

37. The container assembly according to claim 36, wherein the abutment is a part of a recess in the one of the opposed walls of the microchamber.

38. The container assembly according to claim 37, wherein a portion of the recess in the one of the opposed walls of the microchamber defines an interior lens face and the outer surface of the vessel proximate to a junction of the main chamber and the microchamber and in viewing alignment with the interior lens face comprising an exterior lens face, a lens thus defined by the lens faces being located for viewing one or more embryos in a catheter during or after retrieval from the microchamber.

39. The container assembly according to claim 19, wherein a portion of the opposed walls of the microchamber and a portion of the main chamber proximate to a junction of the main chamber and the microchamber define an interior lens face in viewing alignment with an exterior lens face, the lens thus defined by the lens faces being located for viewing one or more embryos in the catheter during or after retrieval from the microchamber.

40. The container assembly according to claim 39, wherein the zones adjoining internal walls and a floor of the microchamber include an inclined portion for opposing the formation of fluid vortexes during embryo aspiration.

41. The container assembly according to claim 17, wherein the vessel comprises a main chamber and a microchamber for the flow of biological medium and movement of gametes and/or one or more embryo(s) therebetween, the inner wall surface of the main chamber being generally frustoconical and includes a small end section adjoining and merging into the microchamber, the microchamber being of generally rectangular cross section.

42. The container assembly according to claim 17, wherein the closure device comprises a valve.

43. An intravaginal fertilization and/or culture container assembly, the intravaginal fertilization and/or culture container assembly being configured for intravaginal accommodation and comprising: (i) a vessel for containing a biological medium, as well as gametes and/or one or more embryo(s), the vessel having a $CO_2$ permeable wall, (ii) a closure device for selective access to the interior of the vessel, and (iii) a buffer chamber for containing a $CO_2$ enriched atmosphere and disposed around the vessel, the shell being cooperable with the vessel, the $CO_2$ enriched atmosphere inside the buffer gas chamber being in communication with the $CO_2$ permeable wall for $CO_2$ equilibration in the vessel after removal of the container assembly from a $CO_2$ enriched environment, wherein a $CO_2$ permeable seal is operatively disposed between the vessel and the buffer gas chamber shell for impeding the ingress of liquids into the buffer gas chamber while allowing the entry of the $CO_2$ enriched gas.

44. The container assembly according to claim 43, wherein the buffer chamber has an open condition for communication with a $CO_2$ enriched intravaginal environment and a closed condition for closing off the buffer chamber from the surroundings after removal from the $CO_2$ enriched intravaginal environment, and wherein the shell is mounted relative to the vessel for movement between an open position and a closed position corresponding respectively to the open and closed conditions.

45. The container assembly according to claim 43, wherein a fluidtight seal operatively disposed between the vessel and the shell prevents both inflow of gas through the $CO_2$ permeable seal from the surroundings and outflow of the $CO_2$ enriched gas from the buffer chamber through the $CO_2$ permeable seal in the closed position.

46. The container assembly according to claim 43, wherein the $CO_2$ permeable seal operatively disposed between the vessel and the shell prevents inflow of $O_2$ into the buffer chamber in the closed position.

47. The container assembly according to claim 43, wherein said vessel comprises a main chamber and a microchamber communicating with each other for flow of biological medium therebetween and movement of gametes and/or one or more embryo(s) therebetween, said $CO_2$ permeable seal defining a principal $CO_2$ enriched atmosphere pathway into the buffer chamber and being received on an outer wall of the vessel remote from the microchamber and liquid sealingly engageable with an inner wall surface of the shell.

48. The container assembly according to claim 47, further comprising another $CO_2$ permeable seal having a $CO_2$ inflow rate different from the $CO_2$ inflow rate of the first-mentioned $CO_2$ permeable seal for ready replacement of the first-mentioned $CO_2$ permeable seal.

49. The container assembly according to claim 44, wherein an upper edge of the shell is in sealing engagement with a radially outwardly extending flange at an upper end of the vessel in the closed position of the buffer chamber.

50. The container assembly according to claim 44, wherein said shell has an upstanding locating member on a bottom wall thereof and the vessel has a protruding complementary locating member at the lower end thereof.

51. The container assembly according to claim 50, wherein the vessel in the open condition of the buffer chamber is angularly offset from the vessel in the closed condition of the buffer chamber.

52. The container assembly according to claim 44, wherein a locating member and complementary locating member define two locating positions corresponding respectively to the open and closed positions of the shell, a portion of a lower end part of the vessel being in engagement with the complementary locating member in a first locating position, a portion of the lower end part of the vessel extending beyond the upper part of the complementary locating member in the second locating position.

53. The container assembly according to claim 52, wherein the locating member and complementary locating member have respective cooperable detent means for defining said first and second locating positions.

54. The container assembly according to claim 43, wherein the closure device comprises a valve.

55. A container assembly comprising (i) a vessel for containing a biological medium as well as gametes and/or one or more embryo(s), the vessel having a wall which confines the biological medium, gametes and/or embryo(s) inside the vessel, said vessel wall including a $CO_2$ permeable wall; (ii) a closure device for selective access to the interior of the vessel, and (iii) a buffer gas chamber for containing a $CO_2$ enriched atmosphere and including a shell cooperable with said vessel, the $CO_2$ enriched atmosphere inside the buffer gas chamber being in communication with the $CO_2$ permeable wall for supplying $CO_2$ enriched atmosphere to the contents of the vessel, further comprising a $CO_2$ permeable seal disposed between the vessel and the buffer gas chamber shell so as to impede ingress of liquids into the buffer gas chamber while allowing entry of $CO_2$ enriched atmosphere.

56. The container assembly of claim 55, wherein the container assembly is configured for intravaginal residence.

57. The container assembly according to claim 56, wherein the $CO_2$ permeable seal is adapted to impede the ingress of contaminants.

58. The container assembly according to claim 55, further comprising a fluidtight seal operatively disposed between the vessel and the shell to prevent both ingress and egress of fluids to and from the buffer chamber in the closed position.

59. The container assembly according to claim 55, wherein the closure device comprises a valve.

* * * * *